(12) United States Patent
Hamasaki et al.

(10) Patent No.: US 8,487,144 B2
(45) Date of Patent: Jul. 16, 2013

(54) PROCESS FOR PRODUCING FLUORINATED PROPENE

(75) Inventors: Hideo Hamasaki, Kawagoe (JP); Yasuo Hibino, Shiki (JP)

(73) Assignee: Central Glass Company, Ltd., Ube-shi (JP)

( * ) Notice: Subject to any disclaimer, the term of this patent is extended or adjusted under 35 U.S.C. 154(b) by 139 days.

(21) Appl. No.: 13/062,560

(22) PCT Filed: Sep. 4, 2009

(86) PCT No.: PCT/JP2009/065477
§ 371 (c)(1),
(2), (4) Date: Mar. 7, 2011

(87) PCT Pub. No.: WO2010/029893
PCT Pub. Date: Mar. 18, 2010

(65) Prior Publication Data
US 2011/0172470 A1    Jul. 14, 2011

(30) Foreign Application Priority Data

Sep. 11, 2008 (JP) ................................ 2008-233878

(51) Int. Cl.
*C07C 17/00* (2006.01)
(52) U.S. Cl.
USPC ....................................................... 570/156
(58) Field of Classification Search
USPC ....................................................... 570/156
See application file for complete search history.

(56) References Cited

U.S. PATENT DOCUMENTS

| 5,616,819 A | 4/1997 | Boyce et al. |
| 6,111,150 A | 8/2000 | Sakyu et al. |
| 6,235,951 B1 | 5/2001 | Sakyu et al. |
| 2005/0020862 A1 * | 1/2005 | Tung et al. ................... 570/164 |
| 2009/0099395 A1 | 4/2009 | Sakyu et al. |

FOREIGN PATENT DOCUMENTS

| JP | 8-104655 A | 4/1996 |
| JP | 8-239334 A | 9/1996 |
| JP | 9-194404 A | 7/1997 |
| JP | 10-7604 A | 1/1998 |
| JP | 2008-19243 A | 1/2008 |

OTHER PUBLICATIONS

International Search Report (Form PCT/ISA/210) dated Oct. 20, 2009 with English translation, including Form PCT/ISA/237 (Six (6) pages).
Albert L. Henne et al., "The Preparation and Directed Chlorination of 1,1,1-Trifluoropropane", J. Am. Chem. Soc., May 1942, pp. 1157-1159, vol. 64.
R.N. Haszeldine, "Reactions of Fluorocarbon Radicals. Part VII. Addition to Trifluoromethyl-substituted Acetylenes.", J. Am. Chem. Soc., Mar. 1952, pp. 3490-3498.
R.N. Haszeldine et al., "The Addition of Free Radicals to Unsaturated Systems. Part II. Radical Addition to Olefins of the Type R•CH:CH$_2$.", 1953, pp. 1199-1206.

* cited by examiner

*Primary Examiner* — Jafar Parsa
(74) *Attorney, Agent, or Firm* — Crowell & Moring LLP

(57) ABSTRACT

There is provided according to the present invention a process for producing 1-chloro-3,3,3-trifluoropropene or 1,3,3,3-tetrafluoropropene, including: reacting 1,1,1,3,3-pentafluoropropane with hydrogen chloride in a gas phase in the presence of a solid catalyst. By the use of a specific solid catalyst such as a catalyst in which chromium is supported on alumina or activated carbon or an alumina catalyst, the 1-chloro-3,3,3-trifluoropropene or 1,3,3,3-tetrafluoropropene can be obtained with high yield from the 1,1,1,3,3-pentafluoropropane, which can be commercially available or prepared on an industrial scale.

5 Claims, No Drawings

PROCESS FOR PRODUCING FLUORINATED PROPENE

TECHNICAL FIELD

The present invention relates to a process for producing 1-chloro-3,3,3-trifluoropropene or 1,3,3,3-tetrafluoropropene, both of which are useful as high-performance materials, intermediate raw materials of biogenic active substances, solvents, cleaners, blowing agents, coolants, aerosols, propellants, etchers and the like.

BACKGROUND ART

There have been reported processes for producing 1-chloro-3,3,3-trifluoropropene by dehydrochlorinating 1,1,1-trifluoro-3,3-dichloropropane, that is obtained by chlorination of 1,1,1-trifluoropropane, with an alcoholic alkali (see Non-Patent Document 1), by adding hydrogen chloride to 3,3,3-trifluoropropine (see Non-Patent Document 2), by dehydroiodinating 3-chloro-1,1,1-trifluoro-3-iodopropane with ethanolic potassium hydroxide (KOH) (see Non-Patent Document 3), by fluorinating 1,3,3,3-tetrachloropropene or 1,1,3,3-tetrachloropropene in a pressurized liquid phase without the use of a catalyst (see Patent Document 1), and by fluorinating 1,1,1,3,3-pentachloropropane with hydrogen fluoride in a liquid phase in the presence or absence of a fluorination catalyst (see Patent Documents 2 and 3).

PRIOR ART DOCUMENTS

Non-Patent Documents

Non-Patent Document 1: J. Am. Chem. Soc., 64, 1942, 1158
Non-Patent Document 2: J. Chem. Soc., 1952, 3490
Non-Patent Document 3: J. Chem. Soc., 1953, 1199

Patent Documents

Patent Document 1: U.S. Pat. No. 5,616,819
Patent Document 2: Japanese Laid-Open Patent Publication No. 8-104655
Patent Document 3: Japanese Laid-Open Patent Publication No. 8-239334

SUMMARY OF THE INVENTION

Problems to be Solved by the Invention

The processes of Non-Patent Documents 1 and 3 each involve dehydrohalogenation with alkali decomposition and thus have a problem that there occurs an equivalent molar amount of alkaline metal salt as a waste. The processes of Non Patent Documents 2 and 3 have a problem that it is difficult to get the raw material such as 3,3,3-trifluoropropine or 3-chloro-1,1,1-trifluoro-3-iodopropane in large quantity. The processes of Patent Documents 1 to 3 are advantageous in that the raw material is relatively readily available, but have a problem that it is difficult to increase the selectivity of the target product so that the yield of the target product is low.

Means for Solving the Problems

It is accordingly an object of the present invention to provide a process for producing 1-chloro-3,3,3-trifluoropropene or 1,3,3,3-tetrafluoropropene efficiently on an industrial scale.

The present inventors have made researches on the production of 1-chloro-3,3,3-trifluoropropene or 1,3,3,3-tetrafluoropropene from raw materials that are available on an industrial scale and, as a result, have found that it is possible to produce 1-chloro-3,3,3-trifluoropropene or 1,3,3,3-tetrafluoropropene by mixing and reacting 1,1,1,3,3-pentafluoropropane with hydrogen chloride in the presence of a solid catalyst. The present invention is based on this finding.

Namely, there is provided according to a process for producing 1-chloro-3,3,3-trifluoropropene or 1,3,3,3-tetrafluoropropene, comprising: reacting 1,1,1,3,3-pentafluoropropane with hydrogen chloride in a gas phase in the presence of a solid catalyst.

As the solid catalyst, a metal oxide of at least one metal selected from the group consisting of aluminum, chromium, zirconium, titanium and magnesium is suitable.

A supported catalyst in which a compound of at least one metal selected from the group consisting of aluminum, chromium, titanium, manganese, iron, nickel, cobalt, magnesium, zirconium and antimony, or a mixture thereof, is supported on a carrier is also suitable as the solid catalyst. Further, there can suitably be used as the carrier either a metal oxide of at least one metal selected from the group consisting of aluminum, chromium, zirconium, titanium and magnesium, or an activated carbon.

The 1,1,1,3,3-pentafluoropropane may be fed, in the form of a mixture with 1-chloro-3,3,3-trifluoropropane, to the reaction region. The 1,1,1,3,3-pentafluoropropane fed to the reaction region as the raw material may contain 1,1,1,3,3-pentafluoropropane or 1-chloro-3,3,3-trifluoropropene recovered from the reaction product. Furthermore, at least part of the raw material may be an azeotropic mixture containing 1,1,1,3,3-pentafluoropropane and 1-chloro-3,3,3-trifluoropropene.

It is herein noted that, in the present specification, the chemical name for each particular compound refers to any of all possible isomers of the particular compound or any mixture thereof unless otherwise specified. For example, the 1-chloro-3,3,3-tetrafloropropene refers to cis-1-chloro-3,3,3-trifluoropropene, trans-1-chloro-3,3,3-tetrafluoropropene or a mixture thereof. Similarly, the 1,3,3,3-tetrafluoropropene refers to cis-1,3,3,3-tetrafluoropropene, trans-1,3,3,3-tetrafluoropropene or a mixture thereof.

MODES FOR CARRYING OUT THE INVENTION

The present invention will be described in detail below.

According to the present invention, 1-chloro-3,3,3-trifluoropropene and/or 1,3,3,3-tetrafluoropropene is produced by reacting 1,1,1,3,3-pentafluoropropane with hydrogen chloride in a gas phase in the presence of a solid catalyst.

The 1,1,1,3,3-pentafluoropropane can be prepared as the raw reaction material by any method. One known production method of the 1,1,1,3,3-pentafluoropropane is to react 1,1,1,3,3-pentachloropropane or 1-chloro-3,3,3-trifluoropropene with hydrogen fluoride in a liquid phase or a gas phase in the presence of a catalyst. The 1,1,1,3,3-pentafluoropropane can be prepared by this method on an industrial scale, and purchased and used as the raw reaction material.

The solid catalyst is either a metal oxide, a fluorinated metal oxide or a metal supported catalyst.

The metal oxide is preferably a metal oxide of aluminum, chromium, zirconium, titanium or magnesium. The metal oxide may be a composite metal oxide containing at least one metal selected from the group consisting of aluminum, chromium, zirconium, titanium and magnesium. Further, the metal oxide may be treated with hydrogen fluoride or a fluorine-containing organic compound so as to substitute a part or all of oxygen atoms thereof by a fluorine atom. It is preferable that the metal oxide is fluorine-substituted. Particularly preferred is fluorinated alumina, which can be obtained by fluorination of activated alumina with hydrogen fluorine or a fluorine-containing organic compound. It is noted that, in the present specification, the fluorinated metal oxide in which a part or all of oxygen atoms have been substituted by a fluorine atom by treatment with hydrogen fluoride or a fluorine-containing organic compound is also occasionally simply referred to as the metal oxide.

The metal oxide is commercially available or can be prepared by a known catalyst preparation method. It is feasible, for example, to prepare the metal oxide by precipitating a hydroxide out of an aqueous metal salt solution by pH adjustment treatment with ammonia etc., and then, drying or baking the hydroxide precipitate. The thus-obtained metal oxide may be subjected to pulverization or forming. For example, alumina can be generally prepared by treating an aqueous aluminum salt solution with ammonia etc. and subjecting the resulting precipitate to forming and dehydrating operations. Suitably usable is γ-alumina, which is commercially available as catalyst carriers and drying agents. Titania, zirconia etc. can be prepared in the same manner as above. Commercially available titania, zirconia etc. are also usable. Further, the metal oxide may be prepared in composite metal oxide form by coprecipitation.

The metal supported catalyst can be prepared by using the above metal oxide as a carrier. The kind and amount of a metal supported in the metal supported catalyst and the method of supporting the metal on the carrier can be selected as appropriate based on the knowledge of the field of catalyst technologies.

Specific examples of the carrier are alumina, chromia, zirconia, titania and magnesia. These metal oxides may be fluorinated so as to substitute a part or all of oxygen atoms thereof by a fluorine atom. Among others, alumina is preferred as the carrier. Particularly preferred is fluorinated alumina, which can be obtained by fluorination of activated alumina.

An activated carbon is also suitable as the carrier in the metal supported catalyst. Examples of the activated carbon are: plant-based activated carbons prepared using wood charcoal, coconut shell charcoal, palm shell charcoal, raw ash etc. as raw materials; coal-based activated carbons prepared using peat coal, lignite, brown coal, bituminous coal, anthracite etc. as raw materials; petroleum-based activated carbons prepared using petroleum pitch, oil carbon etc. as raw materials; synthetic resin-based activated carbons prepared using polyvinylidene chloride etc. as raw materials. Any of these activated carbons can be selected for use. For example, coconut shell activated carbon (available under the trade name of Granular Shirasagi G2X, GS3 X, GH2X or XRC from Japan Enviro-Chemicals Ltd. or available under the trade name of PCB from Mitsubishi Chemical Calgon Co., Ltd.) is usable. The form and size of the activated carbon can be selected as appropriate depending on the reactor size. The activated carbon can be in various forms such as a spherical form, a cylindrical form, a fibrous form, a powder form and a honeycomb form.

The metal supported on the carrier is preferably one kind of metal or two or more kinds of metals selected from the group consisting of chromium, titanium, aluminum, manganese, nickel, cobalt, titanium, iron, copper, zinc, molybdenum, zirconium, niobium, tantalum, iridium, tin, hafnium, vanadium, magnesium, lithium, sodium, potassium, calcium and antimony. Particularly preferred are aluminum, chromium, titanium, manganese, iron, nickel, cobalt, magnesium, zirconium and antimony. Among others, chromium can suitably be used solely or in the form of a composite system such as chromium/aluminum, chromium/titanium or chromium/iron. For preparation of the catalyst, the metal is generally supported in the form of a nitrate, an oxide, a fluoride, a chloride, a fluorochloride, an oxyfluoride, an oxychloride, an oxyfluorochloride etc. It is particularly preferable to use the metal nitrate or metal chloride and, more specifically, chromium nitrate or chromium chloride.

There is no particular limitation on the preparation method of the supported catalyst. In the case where the metal compound to be supported is in a liquid state at ordinary temperatures, it is feasible to adsorb the metal compound onto the carrier by dropping, immersion, spraying or the like. In the case where the metal compound to be supported is in a solid state at ordinary temperatures, it is feasible to adsorb the metal compound on the carrier by dissolving the metal compound in a solvent and immersing the carrier in the solution or spraying the solution to the carrier. The carrier on which the metal compound has been adsorbed and supported is dried by heating and vacuuming, or by heating under vacuum, to remove therefrom excessive solvent, and then, activated with hydrogen fluoride, hydrogen chloride, chloride, chlorofluorocarbon etc. under heating for use as the supported catalyst.

There is also no particular limitation on the solvent as long as the solvent can dissolve therein the metal compound and does not get decomposed during the reaction. Examples of the solvent are: water; alcohols such as methanol, ethanol and isopropanol; ketones such as methyl ethyl ketone and acetone; carboxylic esters such as ethyl acetate and butyl acetate; halogenated compounds such as methylene chloride, chloroform and trichloroethylene; and aromatic compounds such as benzene and toluene. In the case where the metal compound is less soluble in water, the dissolution of the metal compound can be promoted with the addition of a dissolution aid such as acid or alkali.

Regardless of the kind of the catalyst, it is effective to treat the catalyst in the air at a temperature higher than a given reaction temperature before use for the purpose of preventing the composition of the catalyst from changing during the reaction. Further, it is effective to feed a slight amount of additive component such as chlorine, oxygen or dry air into the reactor during the reaction for improvements in catalyst life, reaction rate and reaction yield. The amount of the additive component is preferably 100% by volume or less relative to the total amount of the reactant components other than the additive component fed to the reactor. The throughput of the target product is unfavorably decreased if the amount of the additive component exceeds the above range.

The reaction temperature is generally in the range of 80 to 500° C., preferably 150 to 450° C., more preferably 250 to 400° C. If the reaction temperature is lower than 80° C., the reaction is too slow and is thus unpractical. If the reaction temperature exceeds 500° C., the selectivity of the 1-chloro-3,3,3-trifluoropropene or 1,3,3,3-tetrafluoropropene, or the total selectivity of the 1-chloro-3,3,3-trifluoropropene and 1,3,3,3-tetrafluoropropene, is unfavorably lowered due to the generation of a decomposition product.

The mole ratio of the 1,1,1,3,3-pentafluoropropane and hydrogen chloride fed to the reaction region can be changed depending on the reaction temperature, the kind of the catalyst used and the like, but generally ranges from 1/10 to 1/50, preferably 1/1 to 1/10. If the amount of the hydrogen chloride is more than 50 times in mole that of the 1,1,1,3,3-pentafluoropropane, there unfavorably occur problems such as decrease in the throughput of the organic substances in the reactor and interference with the separation of unreacted hydrogen chloride from the reaction product in the discharge gas from the reactor. If the amount of the hydrogen chloride is less than 10 times in mole that of the 1,1,1,3,3-pentafluoropropane, the reaction rate is low because it is stoichiometrically difficult to conduct the reaction. This unfavorably results in decrease in the yield.

In order to prevent a surface of the catalyst from being caulked, the raw material may be fed, together with a gas such as oxygen or air, to the reaction region. Further, the reaction may be performed in the coexistence of an inert gas such as nitrogen, argon or helium in the reaction region. In this case, the volume of the inert gas is less than 1 time the total volume of the organic reactant component and the hydrogen chloride. In the present invention, it is preferable that the inert gas coexists in the reaction region as the coexistence of the inert gas corresponds to a reduced pressure condition. However, if the volume of the inert gas is not less than 1 time the total volume of the organic reactant component and the hydrogen chloride, it is difficult to recover the reaction product and is necessary to provide excessively large equipment so that the process unfavorably deteriorates in productivity.

As mentioned above, the hydrogen chloride is preferably used in the excessive amount during the process of the present invention. Thus, some of the hydrogen chloride remains unreacted in the discharge gas from the reaction system. It is feasible that such unreacted hydrogen chloride could be separated from the reaction product and reused. The unreacted hydrogen chloride may be recovered in the form of hydrochloric acid.

Further, the number of molecules in the reaction system increases during the progress of the reaction. It is thus preferable that the reaction proceeds under atmospheric pressure or reduced pressure. In general, the reaction can be performed at around atmospheric pressure (0.1 Mpa), for example, 0.01 to 1 Mpa. It is desirable to select the temperature and pressure conditions that do not cause liquefaction of the raw organic material compound and hydrogen chloride in the reaction system. The contact time is generally 0.01 to 1000 seconds, preferably 0.1 to 100 seconds, more preferably 1 to 60 seconds.

The reactor can be made of a material resistant to heat and resistant to corrosion by hydrogen fluoride, hydrogen chloride etc. As such a material, stainless steel, Hastelloy, Monel, platinum or the like is preferred. The reactor may alternatively be made of a material with a lining of the above metal.

The discharge gas from the reactor, which contains 1-chloro-3,3,3-trifluoropropene and/or 1,3,3,3-tetrafluoropropene produced by the process of the present invention, is basically purified by any known method.

There is no particular limitation on the purification method. One purification method is to wash with water the reaction product containing therein hydrogen chloride and hydrogen fluoride, neutralize the washed product with an alkaline solution and thereby remove the acidic substances such as hydrogen chloride and hydrogen fluoride from the product, dry the product with zeolite etc., and then, distillate the organic substances. Another purification method is to wash the reaction product containing therein hydrogen chloride and hydrogen fluoride with sulfuric acid and then with water, neutralizing the washed product with an alkaline solution and thereby remove the acidic substances such as hydrogen chloride and hydrogen fluoride from the product, dry the product with zeolite etc., and then, distillate the organic substances. The purification may alternatively be conducted by directly distillating the reaction product containing therein hydrogen chloride and hydrogen fluoride and thereby separating the product component such as hydrogen chloride, hydrogen fluoride, 1-chloro-3,3,3-trifluoropropene and 1,3,3,3-tetrafluoropropene from one another.

The distillation of the organic substances can be performed in a batch system or a continuous flow system. By way of example, the distillation of the organic substances in a continuous flow system with three, first to third distillation columns will be explained below. It is however noted to be understood, from this explanation, one skilled in the art would easily know how to distillate the organic substances in a continuous flow system with more than three distillation columns or in a batch system. The reaction product is first subjected to distillation in the first distillation column, thereby recovering trans-1,3,3,3-tetrafluoropropene of low boiling point (boiling point: −19° C.) from the top of the first distillation column. The bottoms of the first distillation column is then subjected to distillation in the second distillation column, thereby recovering an azeotropic mixture of trans-1-chloro-3,3,3-trifluoropropene and 1,1,1,3,3-pentafluoropropane from the top of the second distillation column. The bottoms of the second distillation column is subjected to distillation in the third distillation column, thereby recovering trans-1-chloro-3,3,3-trifluoropropene. Further, the bottoms of the third distillation column may be repeatedly subjected to distillation to recover therefrom cis-1-chloro-3,3,3-trifluoropropene etc.

One of the target compounds, 1-chloro-3,3,3-trifluoropropene (trans isomer), is azeotropic with 1,1,1,3,3-pentafluoropropane and difficult to purify by distillation. It is thus preferable to improve the reaction rate of the 1,1,1,3,3-pentafluoropropane as much as possible.

The azeotropic mixture of trans-1-chloro-3,3,3-trifluoropropene and 1,1,1,3,3-pentafluoropropane recovered from the second distillation column can be subjected to separation/purification by extractive distillation etc., or can alternatively be returned as the raw material to the reaction system without separation so as to allow conversion of the 1,1,1,3,3-pentafluoropropane to the target compound such as 1-chloro-3,3,3-trifluoropropene or 1,3,3,3-tetrafluoropropene.

EXAMPLES

The present invention will be described in more detail below by way of the following examples. It is noted that these examples are illustrative and are not intended to limit the present invention thereto.

Catalyst Preparation Example 1

Activated alumina ("NKHD-24" produced by Sumitomo Chemical Co., Ltd. with a particle size of 2 to 4 mm and a specific surface of 340 $m^2/g$) was weighed in an amount of 300 g and washed with water so as to remove a powdery substance from a surface of the activated alumina. On the other hand, 10% hydrofluoric acid was prepared by dissolving 115 g of hydrogen fluoride in 1035 g of water. The 10% hydrofluoric acid was gradually added to the washed activated alumina. After stirring, the activated alumina was left still for 3 hours. Subsequently, the activated alumina was washed with water, filtered out, and then, dried at 200° C. in an electric furnace for 2 hours. Further, there was provided a gas-phase reactor in which a cylindrical reaction tube (formed of SUS 316L with a diameter 3.8 cm and a length of 42 cm) had an outer sleeve connected to a heating medium circulation device. In the reaction tube was placed 400 ml of the dried activated alumina. While flowing nitrogen gas through the reaction tube, the temperature of the heating medium was set to 200° C. Hydrogen fluoride was then fed, together with nitrogen gas, into the reaction tube at a hydrogen fluoride-to-nitrogen mole ratio of 1/10 to 1/5 for treatment of the activated alumina with the hydrogen fluoride. Although the temperature of the activated alumina increased during the progress of the treatment, the flow rates and ratio of the hydrogen fluoride and nitrogen gas were controlled in such a manner that the temperature of the activated alumina did not exceed 350° C. The temperature of the heating medium was set to 350° C. at the time of completion of heat generation due to the fluorination treatment, and the flow rates of the hydrogen fluoride and nitrogen gas were maintained for 2 hours. With this, the preparation of the fluorinated alumina catalyst was completed.

Catalyst Preparation Example 2

An aqueous solution was prepared by dissolving 300 g of reagent chemical $Cr(NO_3)_3 \cdot 9H_2O$ in 1 liter of water. In the prepared aqueous solution, 1.8 liter of granular activated carbon having a diameter of 4 to 8 mm, a specific surface of 1200 $m^2/g$ and a pore size of 18 A ("Granular Shirasagi G2X" produced by Japan EnviroChemicals Ltd.) was immersed and set aside for one day. The immersed activated carbon was filtered out, and then, left and dried at 100° C. in a hot-air circulation dryer for one night. Further, there was provided a gas-phase reactor in which a cylindrical reaction tube (formed of SUS 316L with a diameter 3.8 cm and a length of 42 cm) had an outer sleeve connected to a heating medium circulation device. In the reaction tube was placed 400 ml of the above-prepared chromium-supported activated carbon. While flowing nitrogen gas through the reaction tube, the temperature of the heating medium was increased to 300° C. At the time water drain was stopped, hydrogen fluoride was fed together with nitrogen gas into the reaction tube at a hydrogen fluoride-to-nitrogen mole ratio of 1/10 to 10/1 for treatment of the activated carbon with the hydrogen fluoride. The temperature of the heating medium was increased to 350° C. Then, the treatment of the activated carbon with the hydrogen fluoride and nitrogen gas was maintained for 1 hour. With this, the preparation of the chromium supported activated carbon catalyst was completed.

Catalyst Preparation Example 3

An aqueous solution was prepared by dissolving 300 g of reagent chemical $Cr(NO_3)_3 \cdot 9H_2O$ in 1 liter of water. On the other hand, activated alumina was treated by immersion in hydrofluoric acid and dried in the same manner as in Catalyst Preparation Example 1. In the prepared aqueous solution, 1.8 liter of the resulting activated alumina was immersed and set aside for one day. The activated alumina was filtered out, and then, left and dried at 100° C. in a hot-air circulation dryer for one night. Further, there was provided a gas-phase reactor in which a cylindrical reaction tube (formed of SUS 316L with a diameter 3.8 cm and a length of 42 cm) had an outer sleeve connected to a heating medium circulation device. In the reaction tube was placed 400 ml of the above-prepared chromium supported alumina. While flowing nitrogen gas through the reaction tube, the temperature of the heating medium was increased to 300° C. At the time water drain was stopped, hydrogen fluoride was fed together with nitrogen gas into the reaction tube at a hydrogen fluoride-to-nitrogen mole ratio of 1/10 to 10/1 for treatment of the alumina with the hydrogen fluoride. The temperature of the heating medium was increased to 350° C. Then, the treatment of the alumina with the hydrogen fluoride and nitrogen gas was maintained for 1 hour. With this, the preparation of the chromium supported alumina catalyst was completed.

Reference Catalyst Preparation Example 1

There was provided a gas-phase reactor in which a cylindrical reaction tube (formed of SUS 316L with a diameter 3.8 cm and a length of 42 cm) had an outer sleeve connected to a heating medium circulation device. In the reaction tube was placed 400 ml of granular activated carbon having a diameter of 4 to 8 mm, a specific surface of 1200 $m^2/g$ and a pore size of 18 A ("Granular Shirasagi G2X" produced by Japan EnviroChemicals Ltd.). While flowing nitrogen gas through the reaction tube, the temperature of the heating medium was increased to 300° C. At the time water drain was stopped, hydrogen fluoride was fed together with nitrogen gas into the reaction tube at a hydrogen fluoride-to-nitrogen mole ratio of 10/1 for treatment of the activated carbon with the hydrogen fluoride. The temperature of the heating medium was increased to 350° C. Then, the treatment of the activated carbon with the hydrogen fluoride and nitrogen gas was maintained for 1 hour. With this, the preparation of the activated carbon catalyst was completed.

Reaction Example 1

A gas-phase reactor in which a cylindrical reaction tube (formed of SUS 316L with a diameter 3.8 cm and a length of 42 cm) had an outer sleeve connected to a heating medium circulation device was provided. In the reaction tube was placed 400 ml of the fluorinated alumina catalyst prepared in Catalyst Preparation Example 1. Then, 1,1,1,3,3-pentafluoropropane and hydrogen chloride were fed into the reaction tube so as to react the 1,1,1,3,3-pentafluoropropane with the hydrogen chloride. More specifically, the temperature of the reaction tube was set to a reaction temperature of 310° C. while feeding nitrogen gas into the reaction tube at a flow rate of about 200 ml/min. These conditions were maintained until the temperature of the reaction tube became stable. After the temperature of the reaction tube became stable, the 1,1,1,3,3-pentafluoropropane and hydrogen chloride were fed into the reaction tube at feed rates of 0.8 g/min and 0.5 g/min, respectively. The reaction was stabilized after a lapse of 2 hours from the initiation of the supply of the raw materials. For 2 hours from that point, the product gas discharged from the reaction tube was bubbled into water to remove therefrom acidic gaseous components, and then, passed through a dry ice/acetone trap. With this, 49 g of the product was collected. The collected product was analyzed by gas chromatography (using a FID detector). It was shown by the analysis results that the product had a composition of 5.1% (area %, the same applies to the followings) of trans-1,3,3,3-tetrafluoropropene, 1.5% of cis-1,3,3,3-tetrafluoropropene, 1.0% of 1,1,1,3,3-pentafluoropropane, 81.5% of trans-1-chloro-3,3,3-trifluoropropene and 10.1% of cis-1-chloro-3,3,3-trifluoropropene. These results are indicated in TABLE 1.

Reaction Example 2

The reaction of 1,1,1,3,3-pentafluoropropane and hydrogen chloride was carried out in the same manner as in Reaction Example 1, except for setting the feed rate of the hydrogen chloride to 0.3 g/min and for setting the feed rate of the 1,1,1,3,3-pentafluoropropane to 0.5 g/min. The reaction was stabilized after a lapse of 2 hours from the initiation of the supply of the raw materials. For 2 hours from that point, the product gas discharged from the reaction tube was bubbled into water to remove acidic gaseous components, and then passed through a dry ice/acetone trap. With this, 46 g of the product was collected. The collected product was analyzed by gas chromatography. It was shown by the analysis results that the product had a composition of 24.7% of trans-1,3,3,3-tetrafluoropropene, 5.2% of cis-1,3,3,3-tetrafluoropropene, 9.6% of 1,1,1,3,3-pentafluoropropane, 53.3% of trans-1-chloro-3,3,3-trifluoropropene and 6.6% of cis-1-chloro-3,3,3-trifluoropropene. These results are indicated in TABLE 1.

Reaction Example 3

The reaction of 1,1,1,3,3-pentafluoropropane and hydrogen chloride was carried out in the same manner as in Reaction Example 1, except for using 400 ml of the chromium-supported activated carbon catalyst prepared in Catalyst Preparation Example 2 and for controlling the reaction temperature to 280° C. The reaction was stabilized after a lapse of 2 hours from the initiation of the supply of the raw materials. For 2 hours from that point, the product gas discharged from the reaction tube was bubbled into water to remove acidic gaseous components, and then passed through a dry ice/acetone trap. With this, 52 g of the product was collected. The collected product was analyzed by gas chromatography. It was shown by the analysis results that the product had a composition of 0.7% of trans-1,3,3,3-tetrafluoropropene, 0.2% of cis-1,3,3,3-tetrafluoropropene, 1.8% of 1,1,1,3,3-pentafluoropropane, 85.3% of trans-1-chloro-3,3,3-trifluoropropene and 10.0% of cis-1-chloro-3,3,3-trifluoropropene. These results are indicated in TABLE 1.

Reaction Example 4

The reaction of 1,1,1,3,3-pentafluoropropane and hydrogen chloride was carried out in the same manner as in Reaction Example 1, except for using 400 ml of the chromium-supported alumina catalyst prepared in Catalyst Preparation Example 3 and for controlling the reaction temperature to 350° C. The reaction was stabilized after a lapse of 2 hours from the initiation of the supply of the raw materials. For 2 hours from that point, the product gas discharged from the reaction tube was bubbled into water to remove acidic gaseous components, and then passed through a dry ice/acetone trap. With this, 49 g of the product was collected. The collected product was analyzed by gas chromatography. It was shown by the analysis results that the product had a composition of 2.7% of trans-1,3,3,3-tetrafluoropropene, 0.5% of cis-1,3,3,3-tetrafluoropropene, 0.8% of 1,1,1,3,3-pentafluoropropane, 84.5% of trans-1-chloro-3,3,3-trifluoropropene and 10.1% of cis-1-chloro-3,3,3-trifluoropropene. These results are indicated in TABLE 1.

Reaction Example 5

The reaction of 1,1,1,3,3-pentafluoropropane and hydrogen chloride was carried out in the same manner as in Reaction Example 1, except for feeding the hydrogen chloride at a feed rate of 0.5 g/min and for feeding the 1,1,1,3,3-pentafluoropropane and trans-1-chloro-3,3,3-trifluoropropene at feed rates of 0.4 g/min and 0.1 g/min, respectively, as raw organic materials. The reaction was stabilized after a lapse of 2 hours from the initiation of the supply of the raw materials. For 2 hours from that point, the product gas discharged from the reaction tube was bubbled into water to remove acidic gaseous components, and then passed through a dry ice/acetone trap. With this, 52 g of the product was collected. The collected product was analyzed by gas chromatography. It was shown by the analysis results that the product had a composition of 10.5% of trans-1,3,3,3-tetrafluoropropene, 2.2% of cis-1,3,3,3-tetrafluoropropene, 3.8% of 1,1,1,3,3-pentafluoropropane, 75.2% of trans-1-chloro-3,3,3-trifluoropropene and 8.2% of cis-1-chloro-3,3,3-trifluoropropene. These results are indicated in TABLE 1.

Comparative Reaction Example 1

The reaction of 1,1,1,3,3-pentafluoropropane and hydrogen chloride was carried out in the same manner as in Reaction Example 1, except for using 400 ml of the activated carbon catalyst prepared in Reference Catalyst Preparation Example 1 and for controlling the reaction temperature to 280° C. The reaction was stabilized after a lapse of 2 hours from the initiation of the supply of the raw materials. For 2 hours from that point, the product gas discharged from the reaction tube was bubbled into water to remove acidic gaseous components, and then passed through a dry ice/acetone trap. With this, 57 g of the product was collected. The collected product was analyzed by gas chromatography. It was shown by the analysis results that the product had a composition of 0.1% of trans-1,3,3,3-tetrafluoropropene, 99.8% of 1,1,1,3,3-pentafluoropropane and 0.1% of trans-1-chloro-3,3,3-trifluoropropene. These results are indicated in TABLE 1.

TABLE 1

| | | Temperature ° C. | Raw materials | | |
|---|---|---|---|---|---|
| | Catalyst | | Hydrogen chrolide g/min | HFC-245 g/min | Nitrogen ml/min |
| Example 1 | Fluorinated alumina | 310 | 0.8 | 0.5 | 200 |
| Example 2 | Fluorinated alumina | 310 | 0.3 | 0.5 | 200 |
| Example 3 | Cr/C | 280 | 0.8 | 0.5 | 200 |
| Example 4 | Cr/Fluorinated alumina | 350 | 0.8 | 0.5 | 200 |
| Example 5 | Fluorinated alumina | 310 | 0.5 | 0.4 + 0.1* | 200 |
| Comparative Example 1 | Activated carbon | 280 | 0.8 | 0.5 | 200 |

| | Product | | |
|---|---|---|---|
| | g/2 hours | Trans-1,3,3,3-tetrafluoropropene | Cis-1,3,3,3-tetrafluoropropene |
| Example 1 | 49 | 5.1 | 1.5 |
| Example 2 | 46 | 24.7 | 5.2 |
| Example 3 | 52 | 0.7 | 0.2 |
| Example 4 | 49 | 2.7 | 0.5 |
| Example 5 | 52 | 10.5 | 2.2 |
| Comparative Example 1 | 57 | 0.1 | — |

| | Products | | |
|---|---|---|---|
| | 1,1,1,3,3-Pentafluoropropane | Trans-1-chloro-3,3,3-trifluoropropene | Cis-1-chloro-3,3,3-trifluoropropene |
| Example 1 | 1.0 | 81.5 | 10.1 |
| Example 2 | 9.6 | 53.3 | 6.6 |
| Example 3 | 1.8 | 85.3 | 10.0 |
| Example 4 | 0.8 | 84.5 | 10.1 |
| Example 5 | 3.8 | 75.2 | 8.2 |
| Comparative Example 1 | 99.8 | 0.1 | — |

HFC-245: 1,1,1,3,3-pentafluoropropane
*0.4 g/min of 1,1,1,3,3,-pentafluoropropane and 0.1 g/min of trans-1-chloro-3,3,3-trifluoropropene As described above, it is possible in the present invention that: the 1-chloro-3,3,3-trifluoropropene and 1,3,3,3-tetrafluoropropene can be obtained with high yield by the use of the specific catalyst; and the industrially-produced 1,1,1,3,3-pentafluoropropane can be used as the raw material and secured without difficulty. The process of the present invention is therefore particularly effective as an industrial production process.

Although the present invention has been described with reference to exemplary embodiments, it is to be understood that the present invention is not limited to these described embodiments. Various changes and modifications of the exemplary embodiments described above can be made without departing from the scope of the present invention.

The invention claimed is:

1. A process for producing 1-chloro-3,3,3-trifluoropropene or 1,3,3,3-tetrafluoropropene, comprising: reacting 1,1,1,3,3-pentafluoropropane with hydrogen chloride in a gas phase in the presence of a solid catalyst, wherein the solid catalyst is either a metal oxide of at least one metal selected from the group consisting of aluminum, chromium, zirconium, titanium and magnesium, or a supported catalyst in which a compound of at least one metal selected from the group consisting of aluminum, chromium, titanium, manganese, iron, nickel, cobalt, magnesium, zirconium and antimony, or a mixture thereof, is supported on a carrier.

2. The process for producing 1-chloro-3,3,3-trifluoropropene or 1,3,3,3-tetrafluoropropene according to claim 1, wherein the carrier is either a metal oxide of at least one metal selected from the group consisting of aluminum, chromium, zirconium, titanium and magnesium, or an activated carbon.

3. The process for producing 1-chloro-3,3,3-trifluoropropene or 1,3,3,3-tetrafluoropropene according to claim 1, wherein the 1,1,1,3,3-pentafluoropropane is fed, in the form of a mixture with 1-chloro-3,3,3-trifluoropropane, to a reaction region.

4. The process for producing 1-chloro-3,3,3-trifluoropropene or 1,3,3,3-tetrafluoropropene according to claim 1, wherein the 1,1,1,3,3-pentafluoropropane fed to the reaction region as a raw material contains 1,1,1,3,3-pentafluoropropane or 1-chloro-3,3,3-trifluoropropene recovered from a reaction product.

5. The process for producing 1-chloro-3,3,3-trifluoropropene or 1,3,3,3-tetrafluoropropene according to claim 1, wherein at least part of the raw material is an azeotropic mixture containing the 1,1,1,3,3-pentafluoropropane and 1-chloro-3,3,3-trifluoropropene.

* * * * *